United States Patent [19]
Bienhaus et al.

[11] Patent Number: 5,906,947
[45] Date of Patent: May 25, 1999

[54] METHOD FOR THE REPEATED TRANSFER OF LIQUIDS

[75] Inventors: Gerhard Bienhaus, Wielenbach; Hans Lange, Lampertheim; Thomas Walter, Bichl, all of Germany

[73] Assignee: Boehringer Mannheim GmbH, Mannheim, Germany

[21] Appl. No.: 08/996,150

[22] Filed: Dec. 22, 1997

Related U.S. Application Data

[62] Division of application No. 08/489,580, Jun. 12, 1995, Pat. No. 5,821,436.

[30] Foreign Application Priority Data

Jun. 15, 1994 [DE] Germany ............................. 44 20 900

[51] Int. Cl.$^6$ ........................... G01N 1/00; G01N 33/543
[52] U.S. Cl. .................. 436/518; 73/863.21; 73/863.23; 73/864.21; 73/864.22; 73/864.23; 73/864.24; 210/767; 210/500.26; 210/502.1; 210/503; 422/55; 422/58; 422/61; 422/63; 435/287.1; 435/287.2; 435/287.3; 435/810; 436/524; 436/527; 436/528; 436/530; 436/531; 436/805; 436/808; 436/810

[58] Field of Search ............................ 73/863.21, 863.23, 73/864.21, 864.22, 864.23, 864.24; 210/767, 500.26, 502.1, 503, 505, 508, 908; 141/1; 422/63, 55, 56, 58, 61; 435/287.1, 287.2, 287.3, 810, 975; 436/524, 527, 518, 528, 530, 531, 805, 808, 810

[56] References Cited

U.S. PATENT DOCUMENTS 4,933,148  6/1990  Perlman .
4,985,280  1/1991  Scholz et al. .

FOREIGN PATENT DOCUMENTS 0 566 042 A1  10/1993  European Pat. Off. .
0 587 951 A1   3/1994  European Pat. Off. .
0 588 564 A1   3/1994  European Pat. Off. .
2498331        7/1982  France .
9108319        9/1991  Germany .

*Primary Examiner*—Christopher L. Chin
*Attorney, Agent, or Firm*—Nikaido, Marmelstein, Murray & Oram LLP

[57] ABSTRACT

A method for the repeated transfer of liquids from one of several storage containers into a transfer container wherein protective tips are placed onto a tip of a pipette in order to avoid contamination.

18 Claims, 2 Drawing Sheets

METHOD FOR THE REPEATED TRANSFER OF LIQUIDS

This application is a divisional of U.S. Pat. application Ser. No. 08/489,580, filed Jun. 12, 1995, now U.S. Pat. No. 5,821,436.

Subject matter of the invention is a method for the repeated transfer of liquids, a method for the qualitative and quantitative determination of an analyte in a liquid, and a device that is particularly advantageous to implement this method.

Methods for analyzing body fluids in order to diagnose diseases have been known as useful tools for some time now in clinical and medical diagnostics. Recently, the analysis of nucleic acids has also been used as a diagnostic tool. But neither the recently developed decoding of the genetic code of many organisms nor the use of amplification reactions has led to a more common use of the analysis of nucleic acids as a test. Amplification reactions also allow the detection of minute amounts of nucleic acids. When amplifications are carried out according to the PCR principle (e.g. U.S. Pat. No. 4,683,195), the samples must be prepared in a particularly careful manner in order to isolate the nucleic acids as there are many biological substances which may interfere with the function of the polymerase used in this method. Due to the extremely high sensitivity of this method, it is also necessary that carry-over be avoided in this procedure under all circumstances.

EP-A-0 389 063 describes a method for amplifying nucleic acids where the binding of nucleic acids to glass particles in the presence of guanidinium thiocyanate-containing buffers is mentioned as particularly efficient. Moreover, DE-A-41 39 664, DE-A-41 27 276, and WO 93/11221 describe the use of glass fleeces as a separating material where the centrifugation steps involved require, however, special devices. These currently used plastic parts used in the above methods obey to the so-called spin-column method which makes use of centrifugal forces to press the solution through the glass fleece. In this method, a great variation of parts is used as so-called spin-column tubes.

EP-A-0 588 564 describes pipette tips which, at their lower more narrow end, have a membrane to which analytes can be immobilized. This embodiment is particularly susceptible to a carry-over of liquids from one container to another as these liquids can usually not be completely removed from these membranes. When the pipette tip is then brought into contact with a membrane, liquids from another container may easily be transferred into this container.

It is the object of the present invention to provide methods and devices to avoid carry-over of reagents from one test to another. Subject matter of the invention is a method for the repeated transfer of liquids from one or several storage containers into a transfer container, characterized by die following steps:

a) first transfer of a first liquid into a transfer container through a first opening of the transfer container,
b) attaching a protective tip onto the first opening of the transfer container, said protective tip having an opening, and
c) second transfer of a second liquid into the transfer container through the opening of the transfer container and the protective tip.

Another subject matter of the invention is a method for the qualitative and quantitative determination of an analyte which makes use of this method. The fundamental idea underlying this invention is to reduce the carry-over of sample liquids to containers from which reagent solution is taken to be transferred into the sample solution. It is thus possible to reduce contamination when solutions are transferred from reagent bottles. This idea can be applied to any liquid.

Methods for the repeated transfer of liquids from one or several containers are characterized in that certain quantities of a liquid are repeatedly taken from the same container or that quantities of different liquids are repeatedly taken from different containers to be transferred into a transfer container. The containers from which the liquid is taken may be any desired container, e.g. storage container, tubes, or bottles. Sample storage containers are containers which hold a sample liquid, e.g. primary cups or tubes. Reagent storage containers hold liquids which contain components necessary to carry out a chemical reaction, e.g. a detection reaction. In a particularly preferred manner, these containers contain quantities allowing more than 100 reactions to be carried out.

Sample liquids are those liquids which contain an analyte to be determined, e.g. a nucleic acid, a cell, an antigen, an antibody, or the like. Suitable sample liquids are, hence, body fluids, such as blood or urine, or liquids derived therefrom by adding further components or removing certain components, e.g. serum or plasma.

The transfer container into which liquids are transferred preferably has two openings: a first opening through which the liquid is transferred into the transfer container, and a second opening through which the gas or liquid is removed from the transfer container. The first opening of the transfer container has a preferred cross section of 0.1 to 5 mm$^2$ and is preferably smaller than the second opening. The second opening has a preferred cross section between 3 and 20 mm$^2$ and preferably has the form of a defined, standardized hub flange. This hub flange serves to connect the transfer container to an instrument which can be used to remove liquids, e.g. a manual pipetting aide or an automated pipettor. Such instruments to handle liquid quantities are known to the expert, e.g. pipetting instruments manufactured by Tecan. In this case, the transfer container preferably has an upper opening matching the pipetting arm of the Tecan instrument. Owing to the shape of the opening, an essentially conical form of the inside and also of the outside of the container are preferred. With respect to the liquids to be transferred and, if necessary, the reactions carried out with them, the wall of the transfer containers are preferably made of an inert plastic material, e.g. polypropylene, polyethylene, polycarbonate, polyurethane. It is preferred that the interior formed by the inner wall of the container be not capillary. However, in its interior, the transfer container may contain agents necessary for carrying out a reaction. These agents may include chemical reagents, but also materials for the immobilization of individual components of the first liquid, particularly components of the liquid to be detected. Materials for immobilization include tissues made of polyester, polyamide, polycarbonate, cellulose, nitrocellulose, or glass. These materials can, however, also have another outer shape, e.g. beads or fleeces. If nucleic acids are to be immobilized to these materials, the use of glass fleeces is preferred. If other purposes are desired, it is also possible to use materials that are conventionally used in affinity chromatography procedures.

Moreover, the transfer container may feature modifications necessary to fix reagents or immobilization material. If nucleic acids are to be immobilized to a glass fleece, said glass fleece is preferably fixed with the aid of an inert plastic net in direction towards the two openings of the transfer container. The agents present in the transfer container are preferably located at such a distance away from the first opening that contact with the liquids is not made directly upon contacting the opening. It is particularly preferred that these agents be not attached from the outside to the opening of the transfer container.

In a preferred case, the transfer container has the form of a conventional pipette tip. This ensures that the method of the invention can be adapted to pipetting instruments. However, the transfer container also has an area where a protective tip can be attached. This can be done in the same way as the transfer container is attached to the pipetting arm. For this purpose, the outside of the container is also configured to be conical to match the hub flange of the protective tip. The attachment of the protective tip at the transfer container can be further improved by providing a snap in connection.

Figure 1:
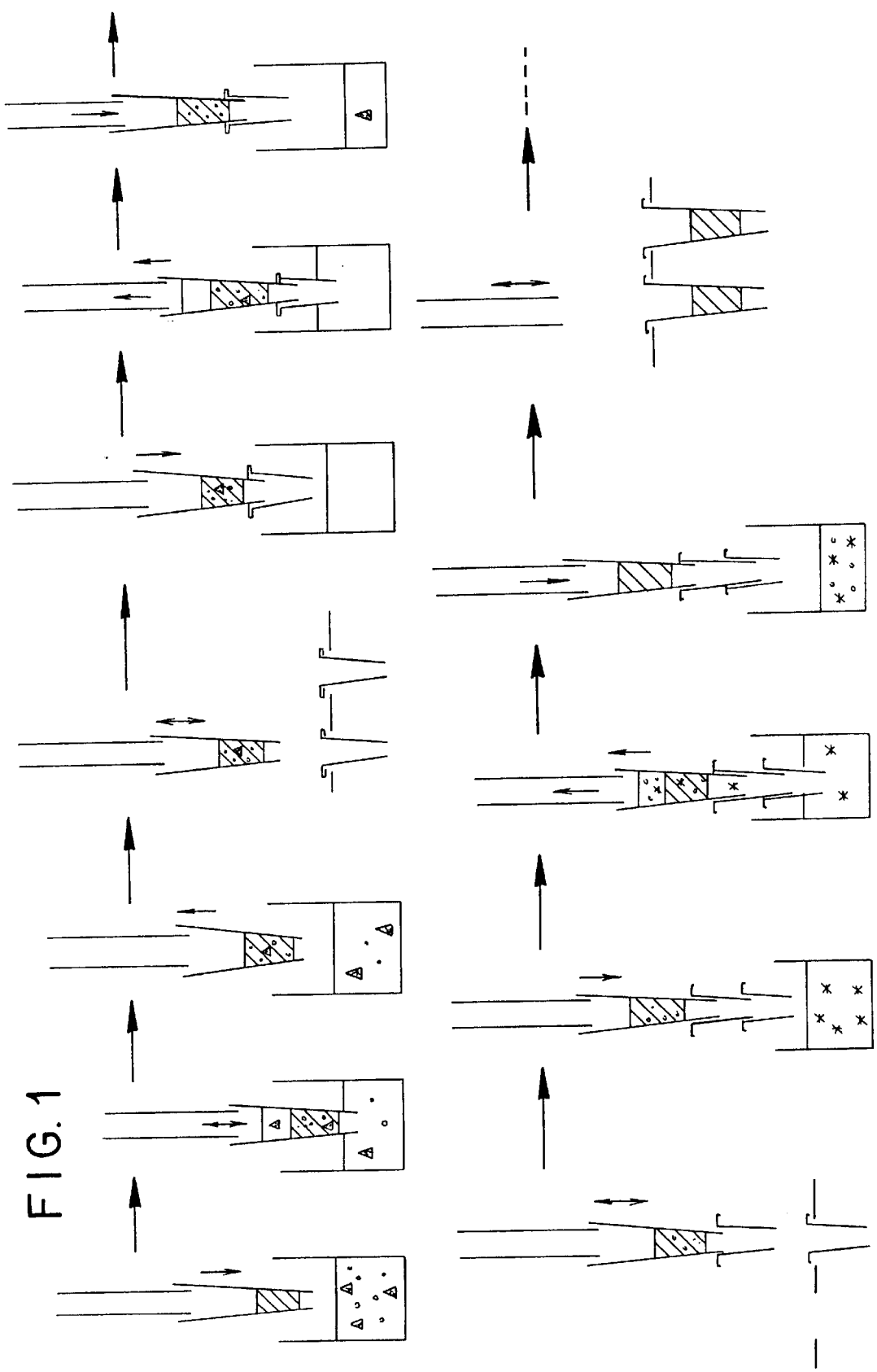
FIG. 1 is a conceptual illustration of a sequence of method steps according to the present invention.

An essential part of the present invention is the use of a protective tip which prevents the outer surface of the transfer container to come into direct contact with the second liquid. This is important in so far that remains of the first liquid may still adhere to the outer surface of the transfer container. These remains could then be transferred into the second liquid and be a source of contamination. Like the transfer container, the protective tip preferably also has two openings of which the first serves to transfer the second liquid from a storage container. The second opening serves as a connection to the transfer container. In a preferred manner, a part of the transfer container which is provided with the first opening projects into the second opening of the protective tip. It is preferred that the protective tip tightly rest against the outer wall of the transfer container to avoid loss of pressure or liquid and to further reduce the risk of contamination. At its end, the protective tip, therefore, has a defined standardized form which matches the outer form of the transfer container in the area of the first opening. Possible material for the protective tip is particularly the one that is also used for the transfer container. In a preferred manner, the protective tip is an inexpensive disposable plastic product. The protective tip can, hence, have a form similar to the one of conventional pipette tips. Its interior can, however, be much smaller than the commonly used pipette tips as the quantity of liquid taken up must not be contained in it. In its interior, the protective tip may contain agents for carrying out a reaction as does the transfer container. However, preferred pipette tips are those which do not contain any such agents.

A typical application of a method where the repeated transfer of liquids from storage container occurs are methods for determining analytes in a sample liquid. In this particular case, contamination is particularly critical as it may falsify the results. Another subject matter of the invention is, hence, a method for the qualitative and quantitative determination of an analyte comprising the following steps:
a) Receiving a sample liquid in which the analyte to be determined is contained through an opening (11) provided in a first transfer container (10)
b) Immobilizing the analyte in the first transfer container (10)
c) Removing the liquid from the transfer container (10)
d) Attaching a protective tip (20) with an opening (21) to the first opening (11) of the transfer container (10)
e) Transferring a second liquid into the transfer container (10) through openings (21, 11).

The following is a description of such an isolation procedure as known from the isolation of nucleic acids. In the description, reference is made to FIG. 1. In a first step, a given volume of a sample liquid is transferred into the transfer container in any desired way. This can be accomplished, for example, by applying a low pressure to the first opening of the transfer container via the second opening of the transfer container (e.g. applying suction by means of a pipetting aid or pipetting instrument, such as manufactured by Tecan, Hamilton or Beckmann). It is possible to apply this low pressure several times to draw in and eject liquid. The opening (11) of the transfer container extends into the sample liquid in the storage container. The transfer container has in its interior a glass fleece that is attached by means of inert plastic nets and spreads over the entire cross section of the transfer container. The sample liquid contains the nucleic acid to be isolated, preferably in a buffer to facilitate immobilization of the nucleic acid to the glass fleece. A preferred buffer is GuSCN. The glass fleece used is a WF 264, WF 265 fleece (manufactured by Whatman). After incubation for 1 sec to 30 min, preferably 2–10 sec, the liquid is ejected from the transfer container into the sample storage container or a waste container. The nucleic acids remain immobilized in the transfer container.

A protective tip is then placed onto the lower tip of the transfer container. These protective tips may be stored in a storage container, e.g. on the pipetting instrument or be automatically mounted in a position selected by the instrument. The lower part of the transfer container which could come into contact with the second liquid is thus protected.

Subsequently, the transfer container can be forwarded into a position where the opening of the protective tip extends into a washing liquid. By absorbing washing liquid from the liquid storage container, remaining sample liquid which may still adhere to the immobilized nucleic acids and contaminate the liquid contained therein, is washed away.

Subsequently, both the washing liquid and the contaminated liquid are ejected into a waste container. The nucleic acids are now immobilized in the transfer container in a relatively pure form.

Then another protective tip is mounted, so that the lower part of the first protective tip is protected by the second protective tip. This prevents liquid which may still adhere to the first protective tip does from coming into contact with the third liquid.

In another step, the transfer container is so immersed into the liquid that the opening of the second tip extends into this liquid. The third liquid is one which causes the nucleic acid to disimmobilize from the glass fleece. This is in particular a liquid with a low salt buffer. As soon as a sufficient amount of liquid was absorbed and the nucleic acids have dissolved, this liquid together with the eluted nucleic acids are poured, after a possible waiting period, into a new container. In this new container, the nucleic acids can be further treated, e.g. subject to a qualitative or quantitative determination. To accomplish this, the container may already contain reagents in a solid or liquid form or such reagents may be added later on.

To complete the method, the transfer container can be taken off the pipetting arm together with the protective tips and be discarded. This is preferably done by the pipetting instrument. In order to carry out another determination a new transfer container is placed on the instrument.

A significant advantage of the method of the invention is that it allows the combination of different tests in the manner described above, depending on whether a transfer container in accordance with the invention or simple pipette tips are placed on the pipetting arm.

Whereas the above-described method proposes to remove the liquid from the lower opening of the transfer container and the protective tips, it is also conceivable that the liquids are discarded from the transfer container through the second opening. This possibility is used in particular when the nucleic acids are immobilized to a solid phase and for the washing steps. It is, however, also possible to draw in the eluted nucleic acids and carry out a measurement in a flow-through meter.

A protective tip can according to the invention be attached, if a contamination should be avoided from the transfer container or the protective tip attached thereto into the (new) liquid container (in case of transfer of a further amount of liquid from the already used liquid container or in case of a transfer of an amount of (new) liquid from a further liquid container). In this way it is for example possible to prevent that parts of already used washing liquid adherent to the transfer container or to the pipette tip are transferred into the new washing liquid and contaminate it. This contamination could yield in incorrect analyses results for analysis performed thereafter using washing liquid from the same washing liquid container.

Figure 2:
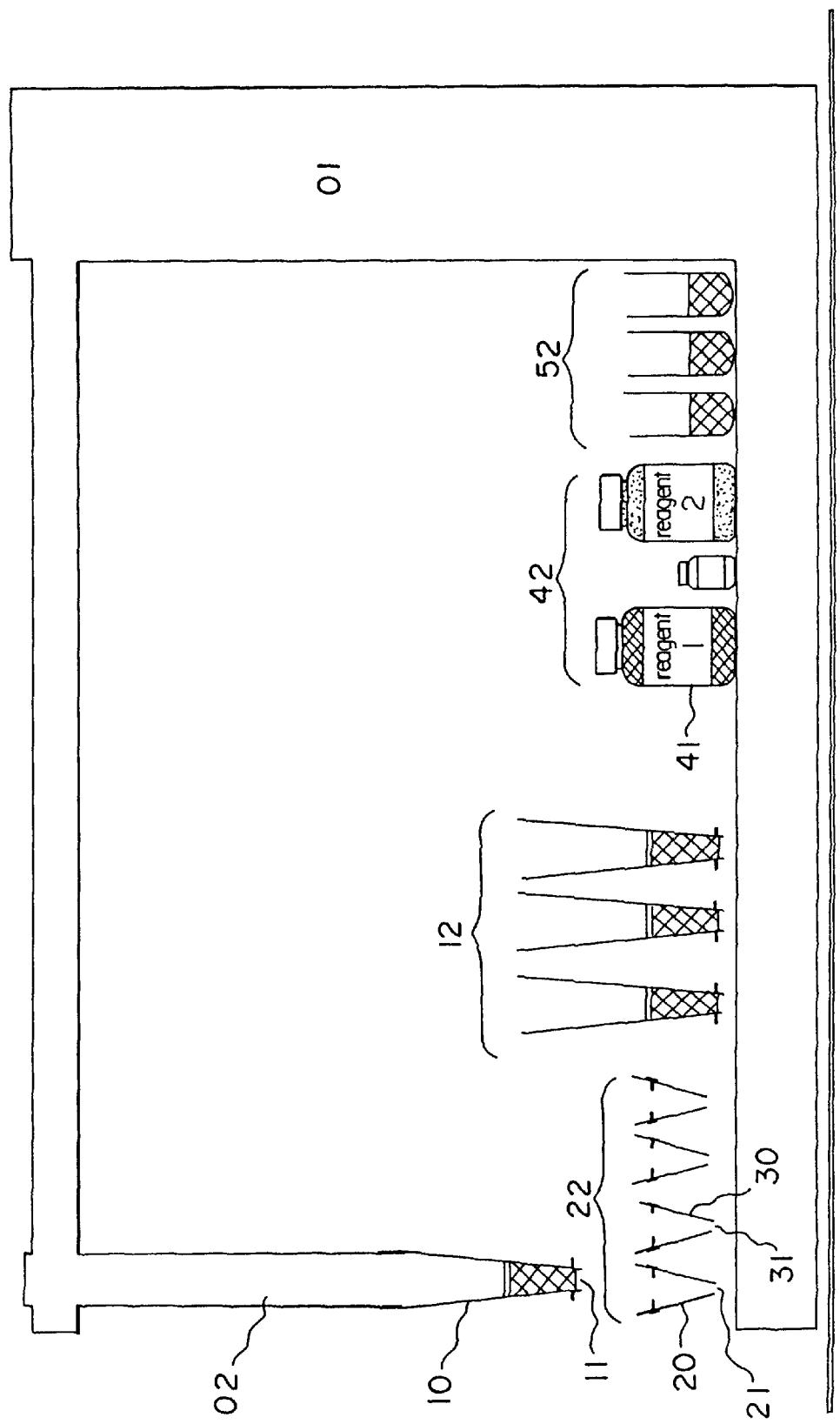
FIG. 2 is a diagrammatic representation of a pipetting instrument for use according to the present invention.

FIG. 2 is a diagrammatic representation showing a pipetting instrument (01) with a pipetting arm (02), transfer containers (10) and (partly) in a magazine (12) protective tips (20), and in a magazine (22) reagents (41) (e.g. washing liquids and elution liquids in a reagent magazine (42)), and sample liquids in sample containers (52).

List of reference numerals
01 Pipetting instrument
02 Pipetting arm
10 Transfer container
11 Opening in 10
12 Magazine for 10
20 Protective tip
21 Opening in 20
22 Magazine for 20
30 Second protective tip
31 Opening in 30
41 Reagents
42 Magazine for 4 liters
52 Sample storage container

We claim:

1. A transfer container in the form of a pipette tip and containing an agent for immobilizing a component of a sample liquid, said transfer container having a first opening therein at the tip thereof, and a protective tip having an opening therein mounted on the tip of the transfer container.

2. A transfer container as recited in claim 1, wherein said transfer container is a plastic pipette tip and said protective tip is a plastic pipette tip.

3. A transfer container a recited in claim 1, wherein said protective tip makes a snap on connection to the transfer container.

4. A transfer container as recited in claim 1, wherein said transfer container contains a glass fleece.

5. A transfer container as recited in claim 1, wherein said first opening has a cross-sectional area of 0.15 mm$^2$.

6. A transfer container as recited in claim 1, wherein said transfer container has inside and outside surfaces which are essentially conical.

7. A transfer container as recited in claim 1, wherein said agent for immobilizing a component comprises at least one material selected from the group consisting of polyester, polyamide, polycarbonate, cellulose, nitrocellulose and glass.

8. A transfer container as recited in claim 1, wherein said agent for immobilizing a component is fixed with an inert plastic net.

9. A kit for the determination of an analyte in a sample liquid, comprising at least one transfer container in the form of a pipette tip and having an opening therein at the tip thereof, the transfer container containing an agent to immobilize the analyte in the transfer container, at least one first protective tip mountable on the tip of the transfer container and having a tip with a first protective tip opening therein, and at least one second protective tip mountable on the tip of the first protective tip and having a tip with a second protective tip opening therein.

10. Kit of claim 9, wherein the first protective tip and the second protective tip are the same shape.

11. Kit of claim 9, further including separately packaged washing liquid and elution liquid.

12. A kit as recited in claim 9, wherein said at least one transfer container is a plastic pipette tip, said at least one first protective tip is a plastic pipette tip, and said at least one second protective tip is a plastic pipette tip.

13. A kit as recited in claim 9, wherein said at least one first protective tip make a snap on connection to the at least one transfer container.

14. A kit as recited in claim 9, wherein said at least one transfer container contains a glass fleece.

15. A kit as recited in claim 9, wherein said opening in said at least one transfer container has a cross-sectional area of 0.1–5 mm$^2$.

16. A kit as recited in claim 9, wherein said at least one transfer container has inside and outside surfaces which are essentially conical.

17. A kit as recited in claim 9, wherein said agent to immobilize the analyte comprises at least one material selected from the group consisting of polyester, polyamide, polycarbonate, cellulose, nitrocellulose and glass.

18. A kit as recited in claim 9, wherein said agent to immobilize the analyte is fixed with an inert plastic net.

* * * * *